United States Patent [19]

Shroy, Jr. et al.

[11] Patent Number: 5,544,215
[45] Date of Patent: Aug. 6, 1996

[54] DIGITAL ANGIOGRAPHY SYSTEM WITH AUTOMATICALLY DETERMINED FRAME RATES

[75] Inventors: Robert E. Shroy, Jr., Willoughby; Donald T. Green, Madison; Steven C. Kapp, Mentor, all of Ohio

[73] Assignee: Picker International, Inc., Highland Heights, Ohio

[21] Appl. No.: 372,458

[22] Filed: Jan. 13, 1995

[51] Int. Cl.⁶ .................................................. H05G 1/64
[52] U.S. Cl. ........................................ 378/98.12; 378/106
[58] Field of Search ............................. 378/8, 4, 95, 97, 378/98.7, 98.11, 98.12, 106, 105, 108, 109, 110–112, 145, 146

[56] References Cited

U.S. PATENT DOCUMENTS

| | | | |
|---|---|---|---|
| 4,942,596 | 7/1990 | Eberhard et al. | 378/109 |
| 5,119,409 | 6/1992 | Nields et al. | 378/106 |
| 5,347,570 | 9/1994 | Haaks | 378/98.12 |

*Primary Examiner*—Don Wong
*Attorney, Agent, or Firm*—Fay, Sharpe, Beall, Fagan, Minnich & McKee

[57] ABSTRACT

A subject is positioned on a patient support (12) between an x-ray source (10) and a radiation detector assembly (14). The x-ray source is gated (36) on or open prior to triggering (38) a video camera (26) of the x-ray detector assembly to generate an electronic frame image representation. The patient support is moved to generate reference images at positions (5, 4, 3, 2, 1) and the resultant reference images are stored in a reference image memory (42). A radiopaque dye is injected adjacent a first position (1) and the x-ray source and camera are triggered at a first rate indicated by a scan program memory (50). The generated images are displayed on a video monitor until a radiologist decides that the radiopaque dye has moved downstream sufficiently that it is time to index to a second position (2). The radiologist presses an index button (68) causing the patient to be indexed. A timer (48) compasses the actual dwell time that images were collected in the first position (1) with a set of reference dwell times (72). In accordance with the comparison, a second frame rate from the scan program memory is incremented or decremented (74). Images are then generated in the second position with the adjusted second frame rate. This process is repeated for each of a plurality, e.g., five or six positions.

15 Claims, 2 Drawing Sheets

DIGITAL ANGIOGRAPHY SYSTEM WITH AUTOMATICALLY DETERMINED FRAME RATES

BACKGROUND OF THE INVENTION

The present invention relates to the art of angiographic examinations. It finds particular application in conjunction with angiographic examinations of a patient's abdomen and lower extremities with x-rays in which the x-ray source/detector and the patient move relative to each other and will be described with particular reference thereto. However, it is to be appreciated that the present invention will find application in other angiographic examinations or examinations of other moving substances.

Heretofore, digital x-ray systems have been used for angiographic examinations. An x-ray source was disposed on one side of the patient and an x-ray detector disposed on the other side. The x-ray detector converted x-rays which had passed through the patient into visible light which was converted to a digital video signal. Because blood is relatively transparent to x-rays, the patient was injected with a radiopaque dye which had relatively good x-ray absorption such that blood vessels showed up dark in the resultant image. Images of the circulatory system only were made by subtracting a processed reference or basis image taken before injection of the dye from the processed image taken after injection of the dye.

One application of x-ray angiography is imaging blood flow in a patient's lower extremities. The radiopaque dye is introduced into an artery in the pelvic area and flows with the blood through the patient's leg. In a normal healthy patient with good circulation, the dye moves from the pelvic area to the toes quickly, perhaps in 15 seconds. However, in a patient with arterial blockage, typical candidates for such a procedure, the radiopaque dye may require a minute or so to traverse the same course. The travel duration is relatively predictable from the preliminary diagnosis of the patient's condition.

In the prior systems, the x-ray source/detector and patient were moved relative to each other and a series of images were taken along the length of the leg at perhaps five or six positions. Ideally, the images at each position or station were collected as the peak of the radiopaque dye passed through the center of the imaged region. In this manner, images with peak blood opacity were sought at each position. One of the difficulties was gauging when to collect the image without over-irradiating the subject and any nearby medical personnel.

One technique for limiting x-ray exposure while assuring meaningful images was to preprogram the x-ray exposure rates. To assure that an image was collected near the maximum opacity in fast moving blood regions such as near the pelvis, a relatively high frame or image rate was needed, e.g., 3–4 frames/second. As the blood flow slows, subsequent positions have lower frame rates, typically down to about 0.5 frames/second, i.e. 1 frame every 2 seconds. The frame rates used at each location were predetermined prior to the examination. These rates were estimates based on experience and expected pathology.

By reducing the number of frames in the areas of slower blood flow, radiation dosage is reduced. One disadvantage of using predetermined scanning programs is that unexpected blood flow can result in a failure to image when the arteries show maximum opacification. Images with partial opacification are of less diagnostic value than those with maximum opacification. If images are taken with substantially no radiopaque dye present, the procedure normally needs to be repeated with a different set of predetermined frame rates. Repeated injection of radiopaque dye is undesirable because of possible effects on the kidneys which must remove the dye from the blood.

A second disadvantage is that the predetermined frame rates are usually found to be too high, because they should be able to capture maximum opacification in the cases with highest expected flow rates. Patient dose could be reduced if frame rates were not set for the worst case.

The present invention provides a new and improved imaging method and system which overcomes the above problems and others.

SUMMARY OF THE INVENTION

In accordance with the present invention, an angiographic system is provided in which the subject and the diagnostic imaging equipment move relative to each other through a plurality of positions. At each position, resultant image characteristics and acquisition parameters are analyzed and the data acquisition characteristics at the next position are adjusted accordingly.

In accordance with a more specific aspect of the present invention, the attending radiologist manually controls movement from position to position. The dwell time at each position is compared to a set of preselected dwell times. A data acquisition frame rate at a next position is adjusted in accordance with the dwell time at the preceding position. More specifically to the preferred embodiment, the frame rate is increased or decreased.

In accordance with another aspect of the present invention, the images taken at each station are analyzed and used to adjust the timing and rate of image acquisition at subsequent stations.

One advantage of the present invention is that it reduces x-ray dosages. If blood flow is found to be slow, exposure rates are decreased.

Another advantage of the present invention is that it optimizes the handling of patients with unexpected blood flow rates. Optimal imaging is attained even when unexpected blockages or unexpectedly high blood flow rates are encountered. Also, repeated injection of radiopaque dye may be avoided.

Another advantage of the present invention is that it makes dynamic, real time adjustments during an examination procedure.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
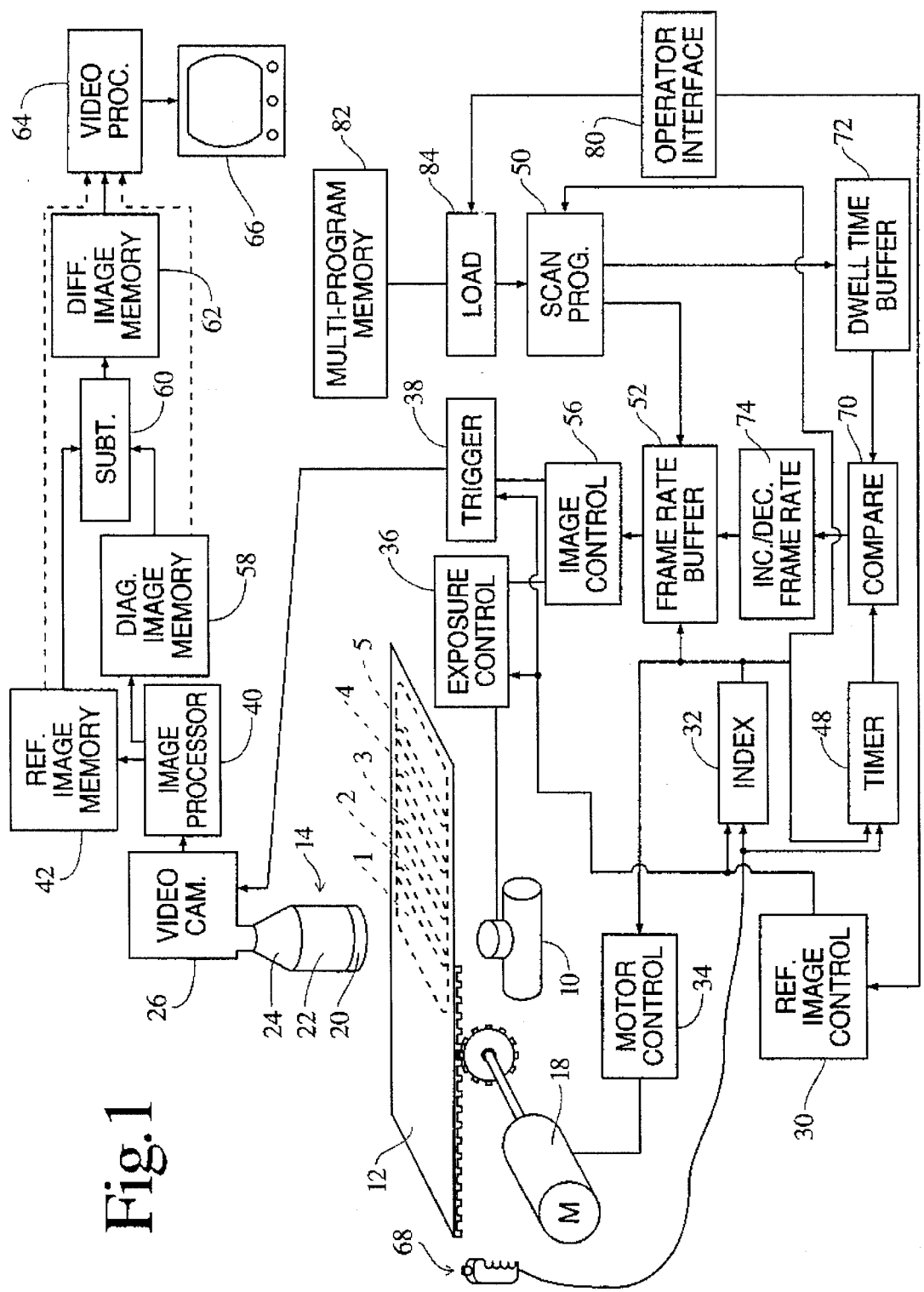
FIG. 1 is a diagrammatic illustration of a digital angiographic system in accordance with the present invention; and, FIG. 2 illustrates an alternate control embodiment.

An x-ray source 10 such as an x-ray tube selectively passes a beam of radiation through a subject support 12 to an x-ray detector assembly 14. The x-ray tube is controlled electronically to stop and start the generation of x-rays.

The x-ray source and x-ray detector combination are mounted for movement relative to the subject supported on the patient support 12. In the preferred embodiment, a motor is selectively indexes the patient support to a series of positions or stations. The exact number of positions is determined from the length of the area to be imaged relative to the size of the x-ray beam and the radiation detector. Typically, five or six positions are sufficient to image from a human patient's pelvis to foot. Alternately, the x-ray source and x-ray detector assembly can be connected to a common frame which is moved mechanically relative to a stationary patient support. Moving the x-ray source and detector tends to be a heavier, more mechanically complex operation than moving the subject. On the other hand, a subject, particularly a human subject with excess fat, tends to oscillate after the patient support is stopped.

The radiation detector assembly includes a phosphor 20 of an image intensifier 22 disposed behind an optically opaque but radiation transparent shield. The phosphor converts received radiation into a relatively faint optical image. The phosphor is part of an image intensifier 22 that boosts the intensity of the optical image. A lens system 24 focuses the intensified optical image onto the image pick-up surface of a video camera 26. Preferably, the video camera 26 is a digital video camera that produces digital video signals. The video camera is also adapted to be operated a single frame at a time in response to an external trigger signal. Alternately, other opto-electrical converters can be utilized to convert the optical image into an electronic image representation.

In the preferred embodiment, a basis image is collected at each of the preselected positions, five in the illustrated embodiment. A system controller 30 controls an indexing means 32 which, in conjunction with a motor controller 34, sequentially positions the x-ray source/detector and patient at each of the positions. The system controller 30 further causes an electronic exposure to activate the x-ray tube for a preselected exposure duration in each of the five positions. Finally, the system controller controls a video camera trigger circuit 38 which triggers the video camera to collect a single frame image each time the shutter is opened. In this manner, the system controller causes the subject to be indexed to each of the five illustrated positions and at each position, one or more reference images are collected. An image processor 40 receives each of the five reference images and stores them in a reference image memory 42.

As soon as the last reference image is generated, the radiopaque dye is released. In the preferred embodiment, the dye is automatically released by a pressure injector under control of the system controller. Alternately, trained medical personnel release the radiopaque dye into a catheter that has been previously positioned in the appropriate artery in the pelvic area.

When the radiopaque dye has been released, the system controller 30 causes a timer 48 to start timing the dwell time in the first position and the automatic scan procedure is commenced. A scan program memory 50 stores a selected scan routine. The selected scan routine includes a frame rate for each of the positions. The frame rate for the first position is loaded into a frame rate buffer A controller 56 causes the exposure control 36 and the video camera trigger control 38 to take exposures at the frame rate in the frame rate buffer 52. Each frame image from the video camera is passed to the image processor and stored in a diagnostic image memory 58.

In the preferred embodiment, an image subtraction processor 60 subtracts a processed reference image for the first position from each of the processed diagnostic images generated in the first position and loads the generated difference images in a difference image memory 62. A video processor 64 converts the most recent difference image received in the difference image memory into appropriate format for display on a video monitor 66. Sufficient computational power is provided in the image processor image subtraction processor 60, and the video processor that the images are displayed on the video monitor substantially in real time. Alternately, rather than displaying the difference image, the diagnostic images can be conveyed directly to the video processor for display. Generally, the radiopaque dye is sufficiently distinctive that its progress through the blood vessels is readily apparent, even when the surrounding tissue and bones are displayed concurrently in other shades of gray or artificially enhanced colors.

The physician monitors the displayed image on the video monitor 66 until the peak of the radiopaque dye has reached the center of the image or other preselected location as the radiologist may find diagnostically appropriate. When the radiologist decides that it is time for the next scan, a hand-held button 68 is depressed. This stops the timer 48, providing an indication of the actual dwell time in the first position. A controller 70 compares the actual dwell time from timer 48 with the set of projected dwell times from a dwell time buffer 72. Based on this comparison, a frame rate incrementor/decrementor 74 adjusts the frame rate for the second position that is loaded into frame rate buffer 52. This comparison and adjustment occur during the movement to position 2. Various curves, such as an exponentially decreasing curve or the like, can represent the relationship between actual and projected dwell time versus change in frame rate. If the image control circuit 56 is only able to call up a limited repertoire of preselected frame rates, then the relationship may be a series of linear steps such that the adjusted frame rate is always one of the frame rates in the repertoire of the control circuit 56. After the indexing procedure has been completed, a plurality of frame images are collected at the second position.

Each time a frame of video data is collected in the second position, the difference or actual image is displayed on the video monitor 66. The radiologist again depresses the hand trigger 68 to index to the third position. This procedure may be repeated analogously for each of the positions. Alternately, the frame rate can be determined using dwell times at all previous positions.

In the preferred embodiment, a plurality of scan programs can be selected or the scan program can be custom generated. An operator selection or control, such as a keyboard or a mouse 80, is used to select one of a plurality of previously selected scan routines from a scan program memory 82 to be loaded 84 into the scan program memory 50. Alternately, the operator control 80 can be used to select proposed dwell times and frame rates for each of the positions.

Figure 2:
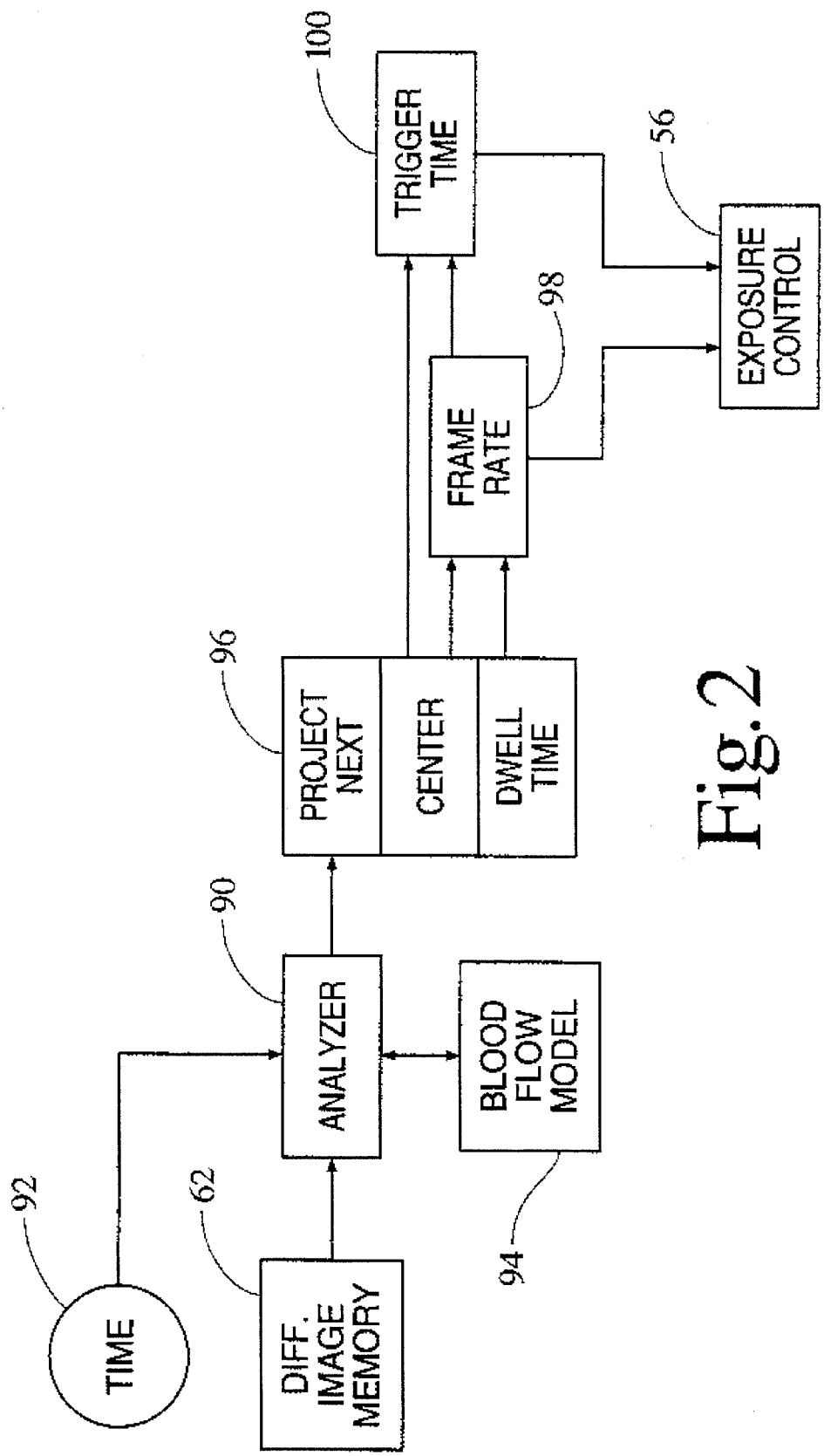

With reference to FIG. 2, rather than relying upon the physician to index to the next position, the resultant images can be analyzed to measure the actual flow rate of the radiopaque dye through the subject. In the embodiment illustrated in FIG. 2, each of the difference images from the difference image memory 62 are analyzed by an image analyzer 90. In one example, the image is divided into strips extending transversely across the patient, generally orthogonal to the direction of blood flow. The lines of pixel data are evaluated for dye concentration. The strip which is most nearly aligned with the peak of the radiopaque dye will integrate to the highest density or darkness. In this manner, the three or so images generated at each position are each transformed to a generally bell-shaped curve, with its peak indicating the location of the peak of the radiopaque dye. From the time at which each image was taken, read from a timer or time buffer 92, and the location of the dye peak in each image, the rate of travel of the radiopaque dye through the currently or just examined region is readily calculable. Based on the progression rate of the radiopaque dye, the time at which the dye peak will arrive at the known center of the next image is predicted. Optionally, a computer memory 94 stores a model of blood flow rate versus position within a patient's leg. This enables the analyzer to adjust the flow rate for normal slowing as the blood moves from the patient's pelvic area toward the patient's foot. From the flow rate calculated by the analyzer, a software routine or processor 96 projects the time at which the peak of the radiopaque dye will reach the center of the next image and the duration of time which will be required for the dye peak to cross the next position. Based on the projected speed of the dye peak in the next position, an algorithm or processor 98 calculates a frame rate which is predicted to generate a preselected number of images, three in the preferred embodiment, as the dye peak is crossing the central region of the image. For example, the frame rate is selected in accordance with the dwell time such that a frame image will be triggered when the dye peak is ⅓, ½, and ⅔ of the way across the next position. A trigger time calculator 100 calculates when triggering of the camera and opening of the shutter is to commence such that the center of the three images is collected at the time at which it is predicted that the dye peak will cross the center of the position.

Again, in the embodiment of FIG. 2, the radiologist sees the difference or actual images substantially in real time on the video monitor and selects when to index to the next position. Thus, if an unexpected blockage occurs, more than the predicted number of frames are collected in a given position. Various other algorithms or routines for adjusting the frame rate and the trigger time for operation of the x-ray tube and camera at the next station are contemplated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of generating diagnostic images at a plurality of overlapping positions along a patient including at least first, second, and third contiguous positions, the method comprising:

selecting at least a first set of reference dwell times during which the diagnostic images are to be generated at the first position and a first selected imaging rate at which the diagnostic images are to be generated at the first position, a second set of reference dwell times over which the diagnostic images are to be generated at the second position, a third set of reference dwell times over which the diagnostic images are to be generated at the third position;

injecting the subject with a radiopaque dye adjacent the first position;

at the first position, generating the diagnostic images at the first imaging rate and displaying the generated diagnostic images on a human-readable display;

manually indexing to the second position in accordance with the human-readable display;

measuring a first actual dwell time over which the diagnostic images are generated at the first position;

comparing the first actual dwell time with the first set of reference dwell times;

adjusting the second imaging rate in accordance with the comparison between the first actual and reference dwell times;

at the second position, generating the diagnostic images at the adjusted second imaging rate and converting the generated images into a human-readable display;

manually indexing to the third position in accordance with the human-readable display;

measuring a second actual dwell time over which images are generated at the second position;

comparing the first and second actual dwell times with the reference dwell times;

adjusting the third imaging rate in accordance with the comparison between the actual and reference dwell times;

at the third position, generating the diagnostic images at the adjusted third imaging rate and converting the generated images into a human-readable display.

2. The method as set forth in claim 1 wherein in each of the steps of generating one of the diagnostic images, an x-ray source is gated open and is closed at the end of generating the diagnostic image, whereby radiation dosage to the subject is minimized.

3. The method as set forth in claim 2 wherein the step of generating electronic image representations includes:

converting radiation which has passed through the corresponding position of the subject into an optical image;

triggering a video camera to convert the optical image into a single frame video image.

4. In an x-ray diagnostic method in which an x-ray source is selectively gated to irradiate and not irradiate a supported subject, an x-ray detector assembly receives x-rays from the x-ray source which have passed through the subject and converts the x-rays into optical images, a video camera converts the optical images into electronic image representations, the video camera which is triggered subsequent to the gating of the x-ray source to irradiate the subject, and in which the subject support and the x-ray source/x-ray detector assembly move relative to each other such that a plurality of positions are selectively examined and at least the x-ray source is gated a plurality of times in each position at a selected gating rate such that a plurality of image representations in each position are generated, THE IMPROVEMENT COMPRISING:

adjusting a frame rate with which the video camera is triggered in accordance with a duration over which image representations were collected at the preceding positions.

5. In an x-ray diagnostic method in which an x-ray source is selectively gated to irradiate and not irradiate a supported subject, an x-ray detector assembly receives x-rays from the x-ray source which have passed through the subject and converts the x-rays into an electronic image representation, and in which the subject support and the x-ray source/x-ray detector assembly move relative to each other such that a plurality of positions are selectively examined and at least the x-ray source is gated a plurality of times in each position at a selected gating rate such that a plurality of image representations in each position are generated, THE IMPROVEMENT COMPRISING:

at a second and subsequent positions, adjusting the rate at which the x-ray source is gated to pass radiation through the subject to generate electronic image representations in accordance with a duration over which image representations were collected at the preceding positions.

6. In the method as set forth in claim 5, the improvement further comprising:

in each position, generating a plurality of electronic image representations and converting the electronic image representations into a human-readable display;

manually indexing to the next position in accordance with images on the human-readable display.

7. In the method as set forth in claim 6, the improvement further comprising:

automatically indexing through each of the plurality of positions to generate a reference image for each position;

injecting a radiopaque dye into the patient adjacent a first of the plurality of positions;

in the first position, gating the x-ray source to irradiate the subject and triggering the video camera to generate electronic image representations at a first, preselected frame rate;

indexing to a second of the plurality of positions at which the x-ray source is to be gated and the video camera is to be triggered at a second preselected rate;

adjusting the second rate in accordance with the image representations generated in the first position.

8. In the method as set forth in claim 7, the improvement further comprising:

subtracting the processed reference image from the first position from each processed image representation generated after injection of the radiopaque dye at the first position.

9. A radiology method comprising:

releasing a radiopaque dye into a subject;

selectively gating an x-ray source to irradiate and not irradiate the subject;

receiving x-rays from the x-ray source which have passed through the subject and converting the x-rays into an electronic image representation;

moving the subject and the radiation source relative to each other to each of a plurality of positions;

gating the x-ray source a plurality of times in each position at a selected gating rate such that a plurality of image representations in each position are generated;

analyzing the electronic image representations to determine progress of the radiopaque dye;

adjusting the rate at which the x-ray source is gated in accordance with the determined progress of the radiopaque dye.

10. In a radiology apparatus which includes a subject support, an x-ray source which is selectively gated to irradiate and not irradiate the supported subject, an x-ray detector assembly for receiving x-rays from the x-ray source which have passed through the subject and converting the x-rays into an electronic image representation, and in which the subject support and the x-ray source/radiation detector assembly are movable relative to each other such that a plurality of overlapping positions are selectively examinable and in which at least the x-ray source dwells at each position for a dwell time while the x-ray source is triggered a plurality of times such that a plurality of the electronic image representations are generated at each position, THE IMPROVEMENT COMPRISING:

a rate adjusting means for adjusting a rate at which the x-ray source is triggered to pass radiation through the subject to generate the electronic image representations in accordance with the dwell time at preceding positions.

11. A radiology apparatus comprising:

a subject support;

an x-ray source which is selectively gated to irradiate and not irradiate the supported subject;

an x-ray detector assembly for receiving x-rays from the x-ray source which have passed through the subject and converting the x-rays into an electronic image representation, (i) the subject support and (ii) the x-ray source and the radiation detector assembly being movable relative to each other such that a plurality of overlapping positions are selectively examinable, the x-ray source being triggered a plurality of times at each position such that a plurality of the electronic image representations are generated at each position;

a video camera connected with the radiation detector for converting the detected radiation into electronic image representations, the video camera being triggered subsequent to the x-ray source;

a rate adjusting means for adjusting a frame rate with which the video camera is triggered in accordance with a duration over which the x-ray source and the video camera were triggered at preceding positions.

12. The radiology apparatus as set forth in claim 11, further comprising:

a monitor for converting the electronic image representations generated at each position into human-readable displays;

a means for manually indexing to a next position in accordance with the human-readable displays on the monitor.

13. The radiology apparatus as set forth in claim 12, further comprising:

a means for automatically indexing through each of the plurality of positions to generate an electronic reference image representation corresponding to each position;

a means for subtracting the electronic reference image representation for each position from each processed electronic image representation generated at the corresponding position to generate an electronic difference image representation for display on the video monitor.

14. In a radiological diagnostic apparatus which includes a patient support, an x-ray source which is selectively gated to irradiate and not irradiate the supported patient, an x-ray detector assembly for receiving x-rays from the x-ray source which have passed through the patient and converting the x-rays into an electronic image representation, and in which the patient support and the x-ray source/radiation detector assembly are movable relative to each other such that a plurality of overlapping positions are selectively examinable and in which at least the x-ray source is triggered a plurality of times at each position such that a plurality of the electronic image representations are generated at each position, THE IMPROVEMENT COMPRISING:

an electronic image analyzer for analyzing the electronic image representations to determine progress of a peak concentration of a radiographic dye through the subject;

a rate adjusting means for adjusting a rate at which the x-ray source is triggered to pass radiation through the patient to generate the electronic image representations in accordance with the determined progress of the radiopaque dye concentration.

15. In the apparatus as set forth in claim 14, the improvement further comprising:

a means connected between the analyzer and the rate adjusting means for projecting when the peak concentration will cross a center of a next position.

* * * * *